United States Patent [19]  [11]  4,336,399
Isshiki et al.  [45]  Jun. 22, 1982

[54] PROCESS FOR PRODUCING CARBOXYLIC ACIDS AND/OR ESTERS THEREOF

[75] Inventors: Tomiya Isshiki, Tokyo; Yasuhiko Kijima; Yuh Miyauchi, both of Matsudo, all of Japan

[73] Assignee: Mitsubishi Gas Chemical Company, Inc., Tokyo, Japan

[21] Appl. No.: 205,591

[22] Filed: Nov. 10, 1980

Related U.S. Application Data

[63] Continuation of Ser. No. 946,525, Sep. 26, 1978, abandoned.

[30] Foreign Application Priority Data

Sep. 29, 1977 [JP] Japan ................................ 52-117171

[51] Int. Cl.³ .................. C07C 67/36; C07C 69/76; C07C 51/12
[52] U.S. Cl. ............................... 560/61; 560/105; 560/114; 560/187; 560/204; 560/232; 562/406; 562/519; 260/410; 260/410.9 R; 260/413
[58] Field of Search ............... 560/232, 200, 204, 114, 560/105, 61, 187; 562/406, 519; 260/410, 410.9, 413

[56] References Cited

U.S. PATENT DOCUMENTS

| | | | |
|---|---|---|---|
| 2,650,245 | 8/1953 | Boaden et al. | 560/232 |
| 2,650,246 | 8/1953 | Boaden et al. | 562/519 |
| 2,730,546 | 1/1956 | Reppe et al. | 562/519 |
| 3,014,962 | 12/1961 | Reppe et al. | 562/519 |
| 3,116,978 | 1/1964 | Manollo et al. | 562/519 |
| 3,992,436 | 11/1976 | Zehner | 562/232 |
| 4,118,589 | 10/1978 | Cassar et al. | 562/519 |
| 4,133,963 | 1/1979 | Holmes | 562/519 |

*Primary Examiner*—Paul J. Killos

*Attorney, Agent, or Firm*—Wenderoth, Lind & Ponack

[57] ABSTRACT

A process for producing a carboxylic acid and/or its ester, which comprises reacting an alcohol or ether with carbon monoxide in the presence of elemental nickel or a nickel compound, iodine or an iodine compound and an organic compound of a trivalent nitrogen-group element; wherein the iodine or iodine compound is selected from the following formulae (I) to (IV), $$RX_n \qquad (I)$$

wherein R represents a hydrogen atom or an alkyl or alkylene group, X represents an iodine or bromine atom, and n is an integer of 1 to 3, at least one of n·X's being an iodine atom, $$I_2 \text{ or } I_3- \qquad (II)$$

$$RCOI \qquad (III)$$

wherein R represents an alkyl group, $$MI_2 \qquad (IV)$$

wherein M represents an alkaline earth metal, and the amount of the iodine or iodine compound is such that the amount of the free iodine or iodine compound not chemically bonded to the nickel or nickel compound or the organic compound of a nitrogen-group element is at least 0.2 mole as elemental iodine per mole of each of the nitrogen-group element compound and the nickel or nickel compound.

8 Claims, No Drawings

PROCESS FOR PRODUCING CARBOXYLIC ACIDS AND/OR ESTERS THEREOF

This is a continuation application of Ser. No. 946,525 filed Sept. 26, 1978, now abandoned.

This invention relates to a process for producing carboxylic acids and/or esters thereof by reacting alcohols or ethers with carbon monoxide.

A typical known method for producing carboxylic acids by the carbonylation of alcohols is the production of acetic acid from methanol and carbon monoxide. For example, U.S. Pat. Nos. 2,729,651 and 2,727,902 and German Pat. Nos. 921,938, 933,148 and 947,469 disclose a so-called Reppe method which comprises reacting alcohols, ethers or esters with carbon monoxide using a transition metal such as iron, cobalt or nickel and a compound of a halogen such as iodine or bromine as a catalyst.

These methods, however, require severe high-temperature high-pressure conditions, and many of them do not give satisfactory yields. In an attempt to overcome these disadvantages, methods have recently been developed which involve the use of a complex of a platinum-group metal typified by rhodium as a catalyst (Japanese Patent Publications Nos. 3331 to 3337/1972 which correspond to U.S. applications Ser. Nos. 701,637 to 701,639, 628,577, 628,578, 628,581 and 628,591). These methods which are catalyzed by platinum-group metal complexes can effect carbonylation under milder conditions than the Reppe method, and can give better yields with less amounts of by-products. Since rhodium and other noble metals used as catalyst in these methods are very expensive, it is necessary in commercial practice to take a measure against the loss of the catalyst by, for example, preventing the noble metal complex from being reduced to the metal in a reducing atmosphere [Chemistry and Industry, 29 (5), p. 376 (1960)].

Accordingly, it is an object of this invention to eliminate the defects of the prior art methods, and provide a process for producing carboxylic acids and/or their esters by the carbonylation of alcohols or ethers under mild conditions using an inexpensive catalyst.

The object of the invention is achieved by a process for producing a carboxylic acid and/or its ester, which comprises reacting an alcohol or ether with carbon monoxide in the presence of elemental nickel or a nickel compound, iodine or an iodine compound and an organic compound of a trivalent nitrogen-group element; wherein the iodine or iodine compound is selected from the following formulae (I) to (IV), $$RX_n \qquad (I)$$

wherein R represents a hydrogen atom or an alkyl or alkylene group, X represents an iodine or bromine atom, and n is an integer of 1 to 3, at least one of n·X's being an iodine atom, $$I_2 \text{ or } I_3^- \qquad (II)$$

$$RCOI \qquad (III)$$

wherein R represents an alkyl group, $$MI_2 \qquad (IV)$$

wherein M represents an alkaline earth metal, and the amount of the iodine or iodine compound is such that the amount of the free iodine or iodine compound not chemically bonded to the nickel or nickel compound or the organic compound of a nitrogen-group element is at least 0.2 mole as elemental iodine per mole of the nitrogen-group element compound and at least 0.2 mole as elemental iodine per mole of the nickel or nickel compound.

Alcohols and ethers which can be advantageously used as starting materials in the present invention are aliphatic alcohols having 1 to 20 carbon atoms, aliphatic ethers having 2 to 30 carbon atoms, aromatic alcohols having 7 to 20 carbon atoms, and aromatic ethers having 7 to 30 carbon atoms. Specific examples of these alcohols and ethers include methanol, ethanol, propanol, butanol, pentanol, hexanol, decanol, ethylene glycol, propylene glycol, butanediol, hexanediol, cyclohexanol, benzyl alcohol, phenethyl alcohol, dimethyl ether, diethyl ether, dipropyl ether, methyl ethyl ether, cyclohexyl methyl ether, anisole, phenetole, methyl benzyl ether, methyl cellosolve, butyl cellosolve, monoglyme and diglyme.

Elemental nickel and organic or inorganic nickel compounds can be used as the nickel or nickel compounds (nickel component) which is one catalyst component. There can be used, for example, nickel powder, and various nickel compounds such as nickel acetate, nickel iodide, nickel acetyl acetone, nickel carbonyl, nickel dicarbonyl, nickel dicarbonyl bistriphenyl phosphine, and nickel tetramethyl ammonium iodide.

The iodine and iodine compound (iodine component) is selected from substances represented by the formulae (I) to (IV). Specific examples include $I_2$, $KI_3$, $HI$, $CH_3I$, $C_2H_5I$, $C_3H_7I$, $C_4H_9I$, $CH_2I_2$, $C_2H_4I_2$, $CH_2IBr$, $CHI_3$, $C_2H_4IBr$, $CH_3COI$, $C_2H_5COI$, and $CaI_2$.

The organic compound of a trivalent nitrogen-group element (nitrogen-group component) used in this invention denotes an organic compound of trivalent nitrogen, phosphorus, arsenic or antimony. Examples of the organic nitrogen compound are organic nitrogen compounds of the formula (V)

 (V)

wherein $R_1$, $R_2$ and $R_3$ are identical or different, and each represents a hydrogen atom, an alkyl or aryl group, such as monomethylamine, dimethylamine, butylamine, trimethylamine, diethylamine, aniline and dimethylaniline; and organic nitrogen compounds represented by the following formula (VI)

 (VI)

wherein $R_1$, $R_2$ and $R_3$ are identical or different, and each represents a hydrogen atom or an alkyl or aryl group, such as dimethyl acetamide and methyl phenyl acetamide. Heterocyclic nitrogen compounds such as pyridine, hydroxyquinoline and imidazole, nitriles such as acetonitrile, propionitrile, adiponitrile and benzonitrile, or ammonium salts such as ammonium acetate can also be used.

Examples of the phosphorus, arsenic or antimony compounds are those resulting from substituting P, As or Sb for N in the compounds of formula (V) above, such as trimethylphosphine, tributylphosphine, diphenylphosphine, triphenylphosphine, methyldiphenylphosphine, triphenylarsine, and triphenylstibine. Complexes of these with nickel or nickel carbonyl can also be utilized.

Some of the catalysts comprising the three components are known (for example, see U.S. Pat. No. 2,729,651 cited hereinabove). The catalyst used in this invention, however, is characterized by the fact that it should be used in such a proportion that the amount of the free iodine or iodine compound which does not react with either the nickel component or the nitrogen-group component is at least 0.2 mole, preferably at least 0.5 mole, more preferably at least 1 mole, as elemental iodine per mole of each of the organic nitrogen-group component and the nickel component.

In some cases, the iodine or iodine compound used in this invention reacts with the other catalyst ingredients used. For example, there is a possibility that $CH_3I$ reacts with $P\phi_3$ (wherein $\phi$ represents a phenyl group) to form an onium iodide compound, $(CH_3P\phi_3)I$. In this case, it is necessary to use $CH_3I$ in such an amount that the difference resulting from substracting the amount of $CH_3I$ that reacts with $P\phi_3$ from the total amount of $CH_3I$ used is at least 0.2 mole, preferably at least 0.5 mole, more preferably at least 1 mole, as elemental iodine per mole of each of the organic nitrogen-group component and the nickel component.

In other words, the iodine or iodine compound of formula (I), (II), (III) or (IV) should be present as such in the above-specified amount.

When the organic nitrogen-group compound is a nitrile, the iodine or iodine compound is considered to be not reactive with the nitrogen-group compound. Thus, the total amount of the iodine or iodine compound used can be regarded as the amount of the free iodine compound.

It is obvious to those skilled in the art whether or not the iodine or iodine compound reacts with a given species of the organic nitrogen-group compound used in this invention.

When the iodine compound is HI, $I_2$, $I_3^-$ or RCOI, it is assumed that the compound is reactive with the nickel or nickel compound used in this invention. Thus, the amount of the free iodine compound is the difference resulting from subtracting the amount of the iodine compound which is assumed to react with the nickel or nickel compound from the total amount of the iodine compound. Other iodine compounds are not assumed to be reactive with the nickel or nickel compound, and the total amount of such an iodine compound used will be regarded as the amount of the free iodine compound.

Compounds which are formed by the reaction of the iodine or iodine compound with the other catalyst components, for example a nickel compound such as $NiI_2$ or $[(CH_3)_4N]_2NiI_4$ or an onium iodide compound such as $(CH_3P\phi_3)I$ are not included within the definition of the iodine compounds of the invention represented by formulae (I) to (IV).

If the amount of the free iodine compound is less than the above-specified amount, high yields cannot be achieved under mild reaction conditions.

When the nickel compound used in this invention is concurrently a nitrogen-group compound, for example such a compound as nickel dicarbonyl bistriphenyl phosphine or nickel tetramethyl ammonium iodide, it can be used both as a nickel component and a nitrogen-group component. Hence, so long as such a compound is used in the required amounts, another nitrogen-group compound or nickel compound need not be used. In many cases, such a compound is a coordination compound of nickel and the nitrogen-group compound.

The amount of the nickel component used in this invention is generally $10^{-6}$ to 1 mole, preferably $10^{-4}$ to $10^{-1}$ mole, per liter of the starting materials and a solvent (as will be described hereinbelow, the reaction in accordance with this invention can be performed in the presence of solvent) combined. The amount of the nitrogen-group compound required to form a stoichiometric coordination compound with nickel is $10^{-6}$ to 10 moles, preferably $10^{-4}$ to 5 moles, per liter of the starting materials and a solvent combined. As stated hereinabove, the amount of the iodine component is such that the amount of the free iodine or iodine compound is at least 0.2 mole, preferably at least 0.5 mole, more preferably at least 1 mole, as elemental iodine per mole of each of the nickel component and the nitrogen-group component. The concentration of the iodine or iodine compound per liter of the starting materials and a solvent combined is $10^{-6}$ to 20 moles, preferably $10^{-4}$ to 10 moles, as elemental iodine. When the concentration of the catalyst is high, the rate of the reaction tends to increase.

The reaction in accordance with the process of this invention is carried out at a temperature of 50° to 300° C., preferably 100° to 240° C., and a carbon monoxide partial pressure of 0 to 1000 kg/cm²·G, preferably 2 to 200 kg/cm²·G, more preferably 4 to 70 kg/cm²·G.

Carbon monoxide needs not be of high purity, and may contain hydrogen, carbon dioxide, methane, nitrogen, rare gases, water, etc. Hydrogen does not hamper the reaction, and rather tends to stabilize the catalyst. Carbon monoxide of extremely low purity, however, is not preferred because it will increase the pressure of the reaction system.

The use of a solvent is not essential, but preferable, in the process of this invention. Examples of solvents that can generally be used in this invention include organic acids such as acetic acid, propionic acid, butyric acid, octanoic acid, phthalic acid and benzoic acid, organic acid esters such as methyl acetate, ethyl acetate, dimethyl adipate, methyl benzoate, ethyl benzoate, dimethyl phthalate, diethyl phthalate, dioctyl phthalate, phenyl acetate and tolyl acetate, hydrocarbons such as dodecane, hexadecane, benzene, naphthalene and biphenyl, inorganic acid esters such as triphenyl phosphate, tricresyl phosphate, dibutylphenyl phosphate, tetramethyl ortho-silicate and tetrabutyl silicate, ketones such as acetophenone, propiophenone and benzophenone, and phenols such as phenol, cresol, chlorophenol and nitrophenol.

In particular, the organic acids, organic acid esters and phenols tend to increase the affinity of the starting material with the catalyst. Above all, the organic acid phenyl ester has an effect of preventing the generation of water, hydrogen halide, etc. in the reaction and thus the formation of a corrosive atmosphere, and increasing the yield of the final product.

The alcohol as a starting material in this invention can also act as a solvent. However, when methanol, for example, is used, a volatile substance such as dimethyl ether forms at the early stage of reaction. Furthermore, the affinity of the starting material with the catalyst sometimes changes and the condition of the reaction system will be aggravated.

According to the present invention, carboxylic acids or esters thereof can be obtained in good yields by the carbonylation of the corresponding alcohols or ethers (for example, acetic acid from methanol, nonanoic acid from octanol, ethyl propionate from diethyl ether, and phenyl acetate from anisole) under milder reaction conditions than in the prior art methods, and its advantage is very great.

The following examples illustrate the invention more specifically.

EXAMPLE 1

A reaction vessel was charged with 4.2 g of $NiI_2 \cdot 6H_2O$, 35.5 g of $CH_3I$, 5.8 g of triphenylphosphine ($P\phi_3$), 107.7 g of phenyl acetate as a solvent and 21.1 g of methanol as a starting material. The inside of the reactor was pressurized with carbon monoxide to a total pressure of 42 kg/cm²·G (the partial CO pressure 30 kg/cm²·G), and at this pressure and a temperature of 180° C., the reaction was performed to afford a reddish violet solution containing 38.2 g of acetic acid. This corresponded to a yield of 96.1% based on the starting material. Methyl acetate derived from the starting methanol was formed in trace as an impurity, but no substantial amounts of aldehyde, ether, carboxylic acid (except acetic acid), methane, $CO_2$ and other impurities formed. The time (the half period; abbreviated t) which was required to convert 50% of the starting methanol to acetic acid was 80 minutes. The results are shown in Table 1 together with the reaction conditions, the starting material, solvent and catalyst.

EXAMPLES 2 TO 5

The procedure of Example 1 was repeated except that the starting materials, solvents, catalysts and reaction conditions shown in Table 1 were employed (in Example 5, a gaseous mixture of CO and $H_2$ was used). The results are shown in Table 1. Formation of by-products was not noted. (In Example 3, however, 74% of methyl acetate used as a solvent changed to acetic anhydride.)

EXAMPLE 6

The reaction mixture obtained by the reaction of Example 5 was distilled to remove volatile components. Methyl iodide and anisole were added to the distillation residue, and the same reaction as in Example 5 was performed. The results are shown in Table 1.

EXAMPLE 7

The reaction mixture obtained by the reaction of Example 6 was distilled to remove volatile components. Methyl iodide and anisole were added to the distillation residue, and the same reaction as in Example 6 was performed. The results are shown in Table 1.

EXAMPLE 8

The reaction mixture obtained by the reaction of Example 7 was distilled to remove volatile components. Methyl iodide, acetic acid and methanol were added to the distillation residue, and the same reaction as in Example 7 was performed. The results are shown in Table 1.

EXAMPLES 9 TO 25

The procedure of Example 1 was repeated except that the starting materials, solvents, catalysts and reaction conditions shown in Table 1 were employed. Formation of by-products was not observed.

EXAMPLE 26

Diethylene glycol dimethyl ether as a starting material was reacted by the same procedure as in Example 1 using the catalyst and the reaction conditions shown in Table 1. In 300 minutes after the initiation of the reaction, 10.3 g of ethylene glycol diacetate, 57.7 g of diethylene glycol monomethyl ether monoacetate and 57.8 g of diethylene glycol diacetate were obtained. The results are shown in Table 1.

EXAMPLE 27

A reactor was charged with acetic acid as a solvent and the catalyst components indicated in Table 1, and maintained at the temperature and pressure shown in Table 1. Then, 32 g of methanol as a starting material was fed continuously into the reactor over the course of 4 hours at the above temperature and pressure. Two hours later, the reactor was cooled, and the product was analyzed. It was found that 56.3 g (excluding that added as solvent) of acetic acid was obtained. Formation of by-products such as aldehyde, dimethyl ether and high-boiling carboxylic acids was not observed. The results are shown in Table 1.

EXAMPLES 28 TO 37 AND COMPARATIVE EXAMPLES 1 TO 3

The same procedure as in Example 1 was repeated employing the starting materials, solvents, catalysts and reaction conditions shown in Table 1. The reaction time was 3 hours in Comparative Examples 1 and 3, and 5 hours in Comparative Example 2.

TABLE 1

| Example | Starting material (g) | Solvent (g) | Catalyst Nickel compound (g) | Iodine compound (g) | Nitrogen-group compound (g) | Free I/Ni compound | Free I/Nitrogen-group compound | Reaction conditions Temperature (°C.) | Total pressure (kg/cm². G) | Partial CO pressure (partial H₂ pressure) (kg/cm². G) | Half period, t (minutes) | Yield, g (%) | By-product |
|---|---|---|---|---|---|---|---|---|---|---|---|---|---|
| 1 | Methanol 21.1 | Phenyl acetate 107.7 | NiI₂ · 6H₂O 4.2 | CH₃I 35.5 | Pφ₃ 5.8 | 22.8 | 10.3 | 180° C. | 42 | 30 | 80 | 38.2g (96.1%) | Substantially absent |
| 2 | Methanol 32 | Phenyl acetate 107.8 | Ni(CO)₂(Pφ₃)₂ 6.3 | CH₃I 35.5 | | 23.3 | 11.6 | 200 | 31 | 10 | 70 | 58.0 (96.7) | Substantially absent |
| 3 | Methanol 25.6 | Methyl acetate 59.2 | Ni powder 0.58 | CH₃I 35.5 | Pφ₃ 6.6 | 22.7 | 9.0 | 200 | 73 | 43 | 140 | 47.0 (97.9) | Substantially absent |
| 4 | Methanol 32 | Phenyl acetate 51.6 acetic acid 53.2 | Ni powder 0.58 | CH₃I 35.5 | Pφ₃ 5.8 | 23.0 | 10.3 | 200 | 50 | 32 | 60 | 110.5 (95.5) | Substantially absent |
| 5 | Anisole 100 | — | Ni powder 0.58 | CH₃I 32 | Pφ₃ 12.5 | 18.0 | 3.7 | 200 | 55 | 45 (5) | 62 | 122.1 (97.0) | Substantially absent |
| 6 | Anisole 100 | — | — | CH₃I 32 | — | | | | | | 60 | 119.6 (95.0) | Substantially absent |
| 7 | Anisole 100 | — | — | CH₃I 26 | — | | | | | | 61 | 123.4 (98.0) | Substantially absent |
| 8 | Methanol 28 | Acetic acid 61.3 | — | CH₃I 23 | | | | 200 | 60 | 30 (15) | 70 | 111.2 (95.0) | Substantially absent |
| 9 | Methanol 32 | Phenyl acetate 107.7 | Ni powder 0.58 | CH₃I 35.5 | Pφ₃ 5.8 | 23.0 | 10.3 | 200 | 32 | 10 | 35 | 57.6 (96.0) | Substantially absent |
| 10 | Anisole 100 | — | Ni powder 0.58 | CH₃I 32 | Pφ₃ 12.5 | 18.0 | 3.7 | 160 | 55 | 50 | 240 | 125 (99.3) | Substantially absent |
| 11 | Anisole 100 | — | Ni powder 0.58 | CH₃I 16 | Pφ₃ 12.5 | 6.6 | 1.4 | 200 | 55 | 50 | 120 | 123 (97.7) | Substantially absent |
| 12 | Methanol 21.2 | Phenyl acetate 124.5 | Ni powder 0.58 | CaI₂ 36.8 | Pφ₃ 5.8 | 23.0 | 10.3 | 200 | 42 | 30 | 70 | 37.8 (95.1) | Substantially absent |
| 13 | Methanol 21.2 | Phenyl acetate 124.0 | NiI₂ · 6H₂O 24.2 | CH₃I 35.5 | (C₂H₅)₃N 2.23 | 4.0 | 10.3 | 180 | 41 | 30 | 170 | 37.4 (94.1) | Substantially absent |
| 14 | Methanol 26.8 | Phenyl acetate 114 | Nickel acetylacetone 2.57 | CH₃I 35.5 | Pyridine 3.5 | 20.6 | 4.7 | 200 | 45 | 30 | 120 | 48.2 (95.9) | Substantially absent |
| 15 | Methanol 26.8 | Phenyl acetate 114 | Nickel acetylacetone 2.57 | CH₃I 35.5 | (n-C₄H₉)₃P 4.4 | 22.8 | 10.5 | 200 | 45 | 30 | 35 | 48.7 (96.9) | Substantially absent |
| 16 | Methanol | P-Tolyl | Nickel | CH₃I | Pφ₃ | 22.8 | 10.2 | 200 | 45 | 30 | 25 | 48.2 | Substantially |

TABLE 1-continued

| Example | Starting material (g) | Solvent (g) | Catalyst Nickel compound (g) | Iodine compound (g) | Nitrogen-group compound (g) | Free I/ Ni compound | Free I/ Nitrogen-group compound | Reaction conditions Temperature (°C.) | Total pressure (kg/cm². G) | Partial CO pressure (partial H₂ pressure) (kg/cm². G) | Half period, t (minutes) | Yield, g (%) | By-product |
|---|---|---|---|---|---|---|---|---|---|---|---|---|---|
| | 26.8 | acetate 114.0 | acetyl-acetone 2.57 | 35.5 | 5.83 | | | | | | | (95.9) | absent |
| 17 | Methanol 32 Anisole 46 | — | Ni powder 0.58 | CH₃I 35.5 | Pφ₃ 13.1 | 20.2 | 4.0 | 180 | 55 | 40 | 185 | 57 (95) 55 (96) | Substantially absent |
| 18 | Methanol 26.8 | Phenyl acetate 114 | Nickel acetyl-acetone 2.57 | CH₃I 35.5 | (C₂H₅)₂NH 6.4 | 16.2 | 1.9 | 200 | 47 | 30 | 75 | 48.0 (95.5) | Substantially absent |
| 19 | Methanol 26.8 | Phenyl acetate 114 | Nickel acetyl-acetone 2.57 | CH₃I 35.5 | Ammonium acetate 6.8 | 16.2 | 1.8 | 200 | 46 | 30 | 100 | 47.8 (95.1) | Substantially absent |
| 20 | Methanol 25.6 | P-Tolyl acetate 114 | Nickel acetyl-acetone 2.57 | CH₃I 35.5 | Aniline 8.2 | 16.2 | 1.8 | 200 | 46 | 36 | 45 | 46.2 (96.3) | Substantially absent |
| 21 | Methanol 26.8 | Phenyl acetate 114 | Nickel acetyl-acetone 2.57 | CH₃I 35.5 | Dimethyl acetamide 7.7 | 16.2 | 1.8 | 200 | 46 | 30 | 100 | 48.1 (95.7) | Substantially absent |
| 22 | Methanol 26.8 | Phenyl acetate 114 | Nickel acetyl-acetone 2.57 | CH₃I 35.5 | Sbφ₃ 7.8 | 22.8 | 10.3 | 200 | 46 | 30 | 65 | 44.7 (89.0) | Substantially absent |
| 23 | Methanol 26.8 | Phenyl acetate 114 | Nickel acetyl-acetone 2.57 | CH₃I 35.5 | Asφ₃ 6.2 | 23.0 | 11.4 | 200 | 46 | 30 | 70 | 43.7 (86.9) | Substantially absent |
| 24 | Octanol 65 | Phenyl acetate 68 | Nickel acetyl-acetone 2.57 | CaI₂ 36.8 | Pφ₃ 5.8 | 22.8 | 10.3 | 200 | 33 | 30 | | 32.1 | Substantially absent |
| 25 | Methanol 26.8 | Phenyl acetate 114 | Nickel acetyl-acetone 2.57 | CH₃I 35.5 | Adipo-nitrile 4.3 | 25.0 | 6.3 | 200 | 48 | 30 | | 47.4 (94.3) | Substantially absent |
| 26 | Di-ethylene glycol dimethyl ether 107.2 | | Ni powder 0.58 | CH₃I 35.5 | Pφ₃ 5.8 | 23.0 | 10.3 | 200 | 36 | 30 | | 10.3 57.7 57.8 | Substantially absent |
| 27 | Methanol | Acetic | Ni powder | CH₃I | Pφ₃ | 23.0 | 10.3 | 200 | 41 | 30 | | 56.3 | Substantially |

TABLE 1-continued

| Example | Starting material (g) | Solvent (g) | Catalyst Nickel compound (g) | Iodine compound (g) | Nitrogen-group compound (g) | Free I/Ni compound | Free I/Nitrogen-group compound | Temperature (°C.) | Total pressure (kg/cm². G) | Partial CO pressure (partial H₂ pressure) (kg/cm². G) | Half period, t (minutes) | Yield, g (%) | By-product |
|---|---|---|---|---|---|---|---|---|---|---|---|---|---|
| | 32 | acid 60 | 0.58 | 35.5 | 5.8 | 3.0 | 0.5 | 200 | 55 | 50 | 310 | (93.8) | absent |
| 28 | Anisole 100 | — | Ni powder 0.50 | CH₃I 10.4 | Pφ₃ 12.5 | 22.8 | 10.3 | 200 | 44 | 30 | 210 | 116.0 (92.1) | Substantially absent |
| 29 | Diethyl ether 51.8 | Propionic acid 51.8 | Nickel acetyl- acetone 2.57 | C₂H₅I 39 | Pφ₃ 5.8 | 22.8 | 10.4 | 200 | 44 | 30 | 36 | 66.5 (93.1) | Substantially absent |
| 30 | Methanol 25.6 | Phenyl acetate 108.8 | Nickel acetyl- acetone 2.57 | CH₃I 35.5 | PHφ₂ 4.1 | 1.3 | 0.23 | 200 | 54 | 50 | 480 | 46.2 (96.3) | Substantially absent |
| 31 | Anisole 100 | — | Ni powder 0.50 | CH₃I 8.3 | Pφ₃ 12.5 | 10.0 | 4.5 | 200 | 57 | 30 (10) | 45 | 111.8 (88.8) | Substantially absent |
| 32 | Methanol 16.0 | Acetic acid 40 Aceto- phenone 41 | Nickel acetyl- acetone 2.41 | CH₃I 16.2 | Tributyl- amine 3.83 | 10.1 | 5.1 | 200 | 59 | 30 (10) | 100 | 28.8 (96.0) | Substantially absent |
| 33 | Methanol 16.0 | Aceto- phenone 81.6 | Nickel acetyl- acetone 2.41 | CH₃I 16.2 | n-Butyl- amine 1.37 | 10.1 | 5.1 | 200 | 55 | 30 (10) | 100 | 28.4 (94.7) | Substantially absent |
| 34 | Methanol 16.0 | Phenyl acetate 81.6 | Nickel acetyl- acetone 2.41 | CH₃I 16.2 | Dimethyl- aniline 2.27 | 8.2 | 2.0 | 200 | 45 | 20 (10) | 50 | 28.1 (93.7) | Substantially absent |
| 35 | Methanol 16.0 | Phenyl acetate 81.6 | Nickel acetyl- acetone 2.41 | CH₃I 16.2 | 2-Hydroxy- pyridine 3.57 | 10.0 | 4.5 | 200 | 57 | 30 (10) | 45 | 28.4 (94.7) | Substantially absent |
| 36 | Methanol 16.0 | Acetic acid 40 Aceto- phenone 41 | Nickel acetyl- acetone 2.41 | CH₃I 16.2 | Tri-n- hexylamine 5.55 | 9.9 | 4.5 | 200 | 59 | 30 (10) | 110 | 28.3 (94.3) | Substantially absent |
| 37 | Methanol 16.0 | Phenyl acetate 81.6 | Nickel acetyl- acetone 2.41 | CH₃I 16.2 | n-Hexyl- amine 2.10 | 0.0 | 0.0 | 200 | 73 | 50 | Reacted for 3 hrs. | 28.2 (94.0) | |
| Comp. Ex. 1 | Methanol 100 | — | Nickel acetyl- acetone 2.57 | | (CH₃Pφ₃)I 8.5 | | | | | | | Not formed substan- tially | Large amount of dimethyl- ether |

TABLE 1-continued

| Example | Starting material (g) | Solvent (g) | Catalyst | | | Reaction conditions | | | | | | By-product |
| | | | Nickel compound (g) | Iodine compound (g) | Nitrogen-group compound (g) | Free I/ Ni compound | Free I/ Nitrogen-group compound | Temperature (°C.) | Total pressure (kg/cm². G) | Partial CO pressure (partial H₂ pressure) (kg/cm². G) | Half period, t (minutes) | Yield, g (%) | |
|---|---|---|---|---|---|---|---|---|---|---|---|---|---|
| Comp. Ex. 2 | Methanol 100 | | Nickel acetyl-acetone 2.57 | (CH₃)₄NI 75.4 | Pφ₃ 27 | 0 | 0 | 180 | 64 | 50 | Reacted for 5 hrs. | Not formed substantially | |
| Comp. Ex. 3 | Methanol 32 | Propionic acid 74 | Nickel acetyl-acetone 2.42 | Pφ₃ · CH₃I 60.6 | Pφ₃ 12.6 | 0 | 0 | 200 | 64 | 50 | Reacted for 3 hrs. | Not formed substantially | |

What we claim is:

1. A process for producing a carboxylic acid and/or its ester, which comprises reacting an alcohol selected from the group consisting of an aliphatic alcohol having 1 to 20 carbon atoms and an aromatic alcohol having 7 to 20 carbon atoms, or an ether selected from the group consisting of an aliphatic ether having 2 to 30 carbon atoms and an aromatic ether having 7 to 30 carbon atoms, with carbon monoxide in the presence of (1) elemental nickel or a nickel compound, (2) an organic nitrogen compound selected from the group consisting of (a) a compound of the formula

wherein $R_1$, $R_2$ and $R_3$ are identical or different and each represents hydrogen, alkyl or aryl, (b) a heterocyclic compound of trivalent nitrogen, and (c) a nitrile, and (3) iodine or an iodine compound selected from the following formulae (I) to (IV), $$RX_n \qquad (I)$$

wherein R represents a hydrogen atom or an alkyl or alkylene group, X represents an iodine or bromine atom, and n is an integer of 1 to 3, at least one of n·X's being an iodine atom, $$I_2 \text{ or } I_3{-} \qquad (II)$$

$$RCOI \qquad (III)$$

wherein R represents an alkyl group, $$MI_2 \qquad (IV)$$

wherein M represents an alkaline earth metal; the amount of the iodine or iodine compound being such that the amount of the free iodine or iodine compound not chemically bonded to the nickel or nickel compound or the organic nitrogen compound is at least 0.2 mole as elemental iodine per mole of each of the organic nitrogen compound and the nickel or nickel compound; the reaction being carried out at a carbon monoxide partial pressure of from 4 to 70 kg/cm²·G.

2. The process of claim 1 wherein the amount of the free iodine or iodine compound is at least 0.5 mole as elemental iodine per mole of each of the organic nitrogen compound and the nickel or nickel compound.

3. The process of claim 1 wherein the amount of the organic nitrogen compound is $10^{-6}$ to 10 moles per liter of the starting alcohol or ether.

4. The process of claim 1 wherein the amount of the nickel or nickel compound is $10^{-6}$ to 1 mole per liter of the starting alcohol or ether.

5. The process of claim 1 wherein the amount of the iodine or iodine compound is $10^{-6}$ to 20 moles as elemental iodine per liter of the starting alcohol or ether.

6. The process of claim 3 wherein the reaction is carried out in the presence of a solvent, and the amount of the organic nitrogen compound is $10^{-6}$ to 10 moles per liter of the starting material and the solvent combined.

7. The process of claim 4 wherein the reaction is carried out in the presence of a solvent, and the amount of the nickel or nickel compound is $10^{-6}$ to 1 mole per liter of the starting material and the solvent combined.

8. The process of claim 5 wherein the reaction is carried out in the presence of a solvent, and the amount of the iodine or iodine compound is $10^{-6}$ to 20 moles as elemental iodine per liter of the starting material and the solvent combined.

* * * * *